(12) United States Patent
Hugo et al.

(10) Patent No.: US 7,728,174 B2
(45) Date of Patent: *Jun. 1, 2010

(54) CONTINUOUS HYDROGENATION PROCESSES FOR THE PREPARATION OF XYLYLENEDIAMINES

(75) Inventors: Randolf Hugo, Dirmstein (DE); Kirsten Dahmen, Mannheim (DE); Sabine Huber, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 163 days.

This patent is subject to a terminal disclaimer.

(21) Appl. No.: 11/997,759

(22) PCT Filed: Jul. 27, 2006

(86) PCT No.: PCT/EP2006/064731

§ 371 (c)(1),
(2), (4) Date: Feb. 4, 2008

(87) PCT Pub. No.: WO2007/014901

PCT Pub. Date: Feb. 8, 2007

(65) Prior Publication Data

US 2008/0161609 A1 Jul. 3, 2008

(30) Foreign Application Priority Data

Aug. 2, 2005 (DE) .................. 10 2005 036 222
Dec. 7, 2005 (DE) .................. 10 2005 058 417

(51) Int. Cl.
*C07C 209/48* (2006.01)
(52) U.S. Cl. .................................. 564/385
(58) Field of Classification Search ............ None
See application file for complete search history.

(56) References Cited

U.S. PATENT DOCUMENTS

| | | | |
|---|---|---|---|
| 3,069,469 A | 12/1962 | Wilkes | |
| 3,972,938 A | 8/1976 | Voges et al. | |
| 4,482,741 A | 11/1984 | Kurek | |
| 5,530,127 A | 6/1996 | Reif et al. | |
| 5,696,048 A | 12/1997 | Breitscheidel et al. | |
| 6,297,394 B1 | 10/2001 | Voit et al. | |
| 6,476,267 B1 | 11/2002 | Fuchigami et al. | |
| 7,323,597 B2 * | 1/2008 | Hugo et al. ............... | 564/336 |
| 7,339,080 B2 * | 3/2008 | Hugo et al. ............... | 564/415 |
| 2006/0258889 A1 | 11/2006 | Hugo et al. | |
| 2007/0010693 A1 | 1/2007 | Hugo et al. | |
| 2007/0027345 A1 | 2/2007 | Hugo et al. | |
| 2007/0088178 A1 | 4/2007 | Hugo et al. | |
| 2007/0088179 A1 | 4/2007 | Hugo et al. | |

FOREIGN PATENT DOCUMENTS

| | | |
|---|---|---|
| CN | 1285236 | 2/2001 |
| CN | 1285343 | 2/2001 |
| DE | 1074592 | 2/1960 |
| DE | 1119285 | 12/1961 |
| DE | 1259899 | 2/1968 |
| DE | 2164169 | 7/1972 |
| EP | 0696572 | 2/1996 |
| EP | 0742045 | 11/1996 |
| EP | 0963975 | 12/1999 |
| EP | 1193244 | 4/2002 |
| EP | 1193247 | 4/2002 |
| EP | 1262232 | 12/2002 |
| EP | 1279661 | 1/2003 |
| GB | 852972 | 11/1960 |
| GB | 1143390 | 2/1969 |
| JP | 2002205980 | 7/2002 |
| JP | 2003327563 | 11/2003 |
| WO | WO-99/44984 | 9/1999 |
| WO | WO-00/46179 | 8/2000 |
| WO | WO-2005/026098 | 3/2005 |
| WO | WO-2005/026099 | 3/2005 |
| WO | WO-2005/026100 | 3/2005 |
| WO | WO-2005/026101 | 3/2005 |
| WO | WO-2005/026102 | 3/2005 |
| WO | WO-2005/026103 | 3/2005 |
| WO | WO-2005/026104 | 3/2005 |
| WO | WO-2005/028417 | 3/2005 |
| WO | WO-2006/077233 | 7/2006 |
| WO | WO-2006/089931 | 8/2006 |

OTHER PUBLICATIONS

"MGC-Badger Isophthalonitrile Process," *Process Handbook*, vol. 2, (1976), Japan Petroleum Institute.
"Principles of Chemical Reaction, Engineering and Plant Design," *Ullmann's Encyclopedia of Industrial Chemistry*, Fifth, Completely Revised Edition, vol. B4, pp. 565-569, (1992).

* cited by examiner

*Primary Examiner*—Brian J Davis
(74) *Attorney, Agent, or Firm*—Connolly Bove Lodge & Hutz LLP

(57) ABSTRACT

Processes for preparing a xylylenediamine by continuous hydrogenation, wherein the processes comprise: introducing a liquid circulation stream comprising a phthalonitrile and ammonia into a reactor to continuously hydrogenate the phthalonitrile in the presence of a heterogenous catalyst and the ammonia such that a reactor effluent comprising the xylylenediamine is formed; drawing off a portion of the reactor effluent to provide a first recycle stream; mixing at least a portion of the first recycle stream in a mixing unit with liquid ammonia and fresh phthalonitrile in solid or molten form to provide a second recycle stream; and recycling the second recycle stream to the liquid circulation stream, or wherein the second recycle stream and any remaining unmixed portion of the first recycle stream are both recycled to the liquid circulation stream.

30 Claims, 2 Drawing Sheets

Mixing nozzle radial feed:

or tangential feed:

or

CONTINUOUS HYDROGENATION PROCESSES FOR THE PREPARATION OF XYLYLENEDIAMINES

CROSS-REFERENCE TO RELATED APPLICATIONS

This application is a national stage application, under 35 U.S.C. §371, of PCT/EP2006/064731, filed Jul. 27, 2006, which claims priority of German Patent Application No. 10 2005 036 222.2, filed Aug. 2, 2005, and German Patent Application No. 10 2005 058 417.9, filed Dec. 7, 2005.

BACKGROUND OF THE INVENTION

Xylylenediamine (bis(aminomethyl)benzene) is a useful starting material, for example for the synthesis of polyamides, epoxy hardeners or as an intermediate for preparing isocyanates.

The term "xylylenediamine" (XDA) comprises the three isomers ortho-xylylenediamine, meta-xylylenediamine (MXDA) and para-xylylenediamine.

The term "phthalonitrile" (PN) comprises the three isomers 1,2-dicyanobenzene=o-phthalonitrile, 1,3-dicyanobenzene=isophthalonitrile=IPN and 1,4-dicyanobenzene=terephthalonitrile.

The phthalonitriles are solids (for example isophthalonitrile (IPN) melts at 161° C.) and have relatively poor solubilities in organic solvents.

The two-stage synthesis of xylylenediamine by ammoxidation of xylene and subsequent hydrogenation of the resulting phthalonitrile is known.

Unconverted dinitriles can be removed by distillation from the XDA only with great difficulty.

U.S. Pat. No. 4,482,741 (UOP Inc.) describes the hydrogenation of PN in the presence of ammonia, a specific catalyst and XDA as a solvent.

In MXDA, the solubility of IPN at 70° C. is approx. 20% by weight.

EP-A2-1 193 247 and EP-A1-1 279 661 (both Mitsubishi Gas Chem. Comp.) relate to a process for purifying isophthalonitrile (IPN) and to a process for preparing pure XDA.

EP-A2-1 193 244 (Mitsubishi Gas Chem. Comp.) describes a process for preparing XDA by hydrogenating phthalonitrile which is synthesized in a preceding stage by ammoxidation of xylene, the vaporous product of the ammoxidation stage being contacted directly with a liquid organic solvent (quench) and the resulting quench solution or suspension being sent to the hydrogenation.

Preferred organic solvents are $C_6$-$C_{12}$ aromatic hydrocarbons such as xylene and pseudocumene (column 6, paragraph [0027] and [0028]).

U.S. Pat. No. 3,069,469 (California Research Corp.) teaches, as a solvent for the hydrogenation of aromatic nitriles such as PN, aromatic hydrocarbons, xylene, dioxane and aliphatic alcohols.

DE-A-21 64 169 (Mitsubishi Gas Chemical Co., Inc.) describes, at page 6, last paragraph, the hydrogenation of IPN to meta-XDA in the presence of an Ni and/or Co catalyst in ammonia as a solvent.

GB-A-852,972 (equivalent: DE-A-11 19 285) (BASF AG) discloses the use of ammonia and XDA as solvents in the hydrogenation of PN. The reactant solution is prepared starting from solid PN in an extra step in a separate vessel (cf. page 2, lines 119-120).

JP-A-2003-327563 (Mitsubishi Gas Chem. Co., Inc.) relates to a process for the fixed bed hydrogenation of aromatic dinitriles which are used in the form of 1-10% by weight solutions.

The six patent applications WO-A-05/028417, WO-A-05/026102, WO-A-05/026103, WO-A-05/026104, WO-A-05/026100 and WO-A-05/026101 (BASF AG) each relate to processes for preparing XDA.

In the different processes for preparing phthalonitrile, it is obtained as a solid or dissolved in a solvent, for example pseudocumene, or as a melt. The handling of solvents is typically difficult and laborious. Owing to the low solubility of phthalonitrile in solvents such as o-xylene, m-xylene, p-xylene, pseudocumene, mesitylene, ethylbenzene or methylpyridine, the further processing in a solvent entails very large amounts of solvent which generally have to be removed by distillation after the hydrogenation, which, in accordance with the large streams, entails large apparatus and high energy demands.

Alternatively, an extraction of the PN with water with subsequent distillation is possible. Here too, the energy demands are high, since the water has to be distilled off and the solvent regenerated, at least in a substream.

WO-A-05/026098 (BASF AG) relates to a process for preparing XDA by continuously hydrogenating phthalonitrile over a heterogeneous catalyst in the presence of liquid ammonia in a reactor, in which a portion of the reactor effluent is recycled continuously to the reactor inlet as a liquid circulation stream (circulation mode), in which, by means of a mixing unit, a stream of a phthalonitrile melt is conducted in liquid form into the circulation stream around the hydrogenation reactor, the phthalonitrile conversion in the reactor in single pass being greater than 99% and the circulation stream consisting to an extent of greater than 93% by weight of liquid ammonia and xylylenediamine and not comprising any further solvent for phthalonitrile.

WO-A-05/026099 (BASF AG) relates to a process for preparing XDA by continuously hydrogenating PN over a heterogeneous catalyst in the presence of liquid ammonia in a reactor, a stream of a phthalonitrile melt being mixed in liquid form with a stream of liquid ammonia by means of a mixing unit and the liquid mixture being conducted into the hydrogenation reactor.

Owing to the high melting points, phthalonitriles can be handled in molten form only with difficulty and with a considerable level of complexity for protective heating. For conveying against high pressure, as required in the procedure according to the abovementioned WO-A-05/026098, special pumps are used, for example heatable high-pressure membrane pumps which are firstly very prone to faults and secondly very expensive. However, the process according to WO-A-05/026098 has the advantage that only a comparatively small amount of liquid ammonia has to be worked up, specifically the amount which is discharged with the xylylenediamine reaction product from the reaction stage for workup. The amount of ammonia in the reactor can be selected by means of appropriate selection of the size of circulation, in spite of a small fresh ammonia stream, such that the reaction can proceed under optimal conditions (for example amount of $NH_3$ in mol per mole of phthalonitrile used).

In contrast, in a procedure analogous to the abovementioned WO-A-05/026099, the conveying of the phthalonitrile melt necessitates merely a heatable pump which has to convey the melt into the mixing vessel which is operated at distinctly lower pressure, for example from 20 to 40 bar. To this end, it is possible, for example, to use a less expensive and less fault-prone multistage centrifugal pump. To convey the solution at reactor pressure (e.g. 200 bar) an additional pump is required, but the handling of the solution of phthalonitrile is distinctly simpler and the requirements on the protective heating are considerably smaller. Accordingly, a less expensive pump can be used which is less fault-prone at the lower operating temperature. Especially in the case of shutdowns or operational faults, for example in other parts of the plant too, it is possible to handle the solution better than the melt. However, there is the disadvantage that the solubility of phthalonitrile in ammonia is restricted and temperature-dependent. At lower temperature, the achievable phthalonitrile concentration in ammonia is small but the dissolution vessel can be operated at low pressure, which is also associated with correspondingly low demands on the melt pump. However, this also makes it necessary for a large amount of ammonia, after the hydrogenation of the phthalonitrile, to be worked up again and recovered by pressure distillation. When the temperature in the dissolution vessel is increased, it is possible to set a larger phthalonitrile concentration and less ammonia accordingly has to be worked up. On the other hand, this raises the pressure in the dissolution vessel and the demands for the melt pump and the protective heating rise. The apparatus, machines and equipment become costlier and more fault prone.

BRIEF SUMMARY OF THE INVENTION

The present invention relates to a process for preparing xylylenediamine by continuously hydrogenating phthalonitrile over a heterogeneous catalyst in the presence of liquid ammonia in a reactor.

It was an object of the present invention to discover an improved dissolution process for dissolving phthalonitrile which as far as possible combines the advantages of the two process variants according to WO-A-05/026098 and WO-A-05/026099 outlined and suppresses the disadvantages.

Accordingly, a process has been found for preparing xylylenediamine by continuously hydrogenating phthalonitrile over a heterogeneous catalyst in the presence of liquid ammonia in a reactor, a portion of the reactor effluent being recycled continuously to the reactor inlet as a liquid circulation stream (circulation mode), which comprises, by means of a mixing unit, drawing off phthalonitrile as a melt or in solid form with a stream of liquid ammonia (stream a) and drawing off a further stream which is drawn off at least partly as a substream from the circulation stream around the hydrogenation reactor (stream b), or mixing a mixture of streams a and b and conducting the resulting liquid mixture into the hydrogenation reactor.

BRIEF DESCRIPTION OF THE SEVERAL VIEWS OF THE DRAWING

The foregoing summary, as well as the following detailed description of the invention, may be better understood when read in conjunction with the appended drawings. For the purpose of assisting in the explanation of the invention, there are shown in the drawings representative embodiments which are considered illustrative. It should be understood, however, that the invention is not limited in any manner to the precise arrangements and instrumentalities shown.

In the drawings.

DETAILED DESCRIPTION OF THE INVENTION

Figure 1:
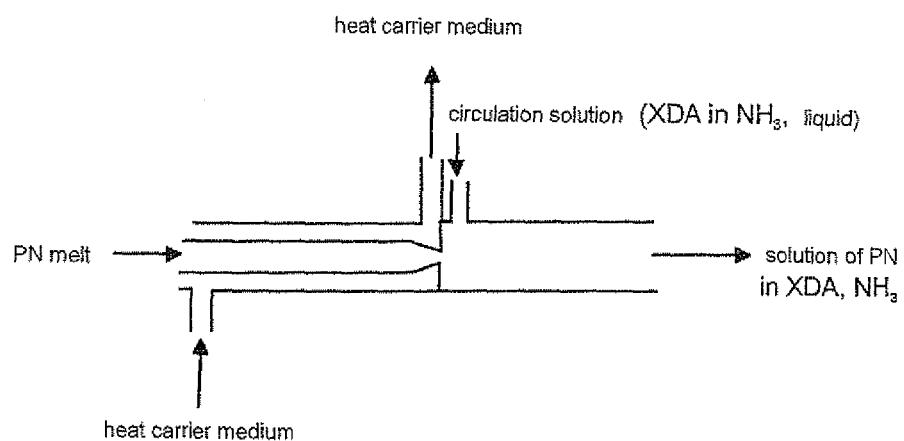
FIG. 1 is a view of a mixing nozzle in accordance with an embodiment of the present invention.

In a particular embodiment of the process according to the invention, the hydrogenation reactor used, for example instead of a single hydrogenation reactor, is a hydrogenation reactor battery.

In that case, the reactor battery consists of 2, 3, 4 or more hydrogenation reactors connected in series. In the circulation mode, a portion of a reactor effluent (for example of the last reactor) is recycled as a liquid circulation stream continuously to a reactor inlet (for example of the first reactor).

The mixing unit is preferably operated at a pressure which is less than the pressure in the reactor.

The circulation stream around the reactor (e.g. stream [11] in FIG. 3) is thus at least partly not recycled directly to the reactor (e.g. as stream [12] in FIG. 3), but rather indirectly (for example as stream [13] in FIG. 3) via the mixing unit. Since the reaction is conducted virtually to full conversion and preference is given to not using any further solvent, the reactor circulation stream consists of a liquid mixture of xylylenediamine, ammonia and any by-products or secondary components.

The process according to the invention preferably finds use for preparing meta-xylylenediamine (MXDA) by hydrogenating isophthalonitrile (IPN) which has in particular been synthesized in a preceding stage by ammoxidation of meta-xylene.

The molten phthalonitrile may come, for example, from a quench attached downstream of an ammoxidation, an evaporation stage or a distillation column, the phthalonitrile being removed, for example, in each case as a melt via the bottom (or side draw) of these thermal separation apparatuses, as described, for example, in WO-A-05/026103 (BASF AG).

Alternatively, it is also possible to use molten PN previously present in solid form in the process according to the invention. The melting can be effected, for example, by means of an extruder.

A further possibility consists in mixing solid phthalonitrile, which is present, for example, in the form of powder, flakes or pellets, continuously, batchwise or semicontinuously in a mixed vessel, (for example stirred vessel) stirred tank or other mixing unit, with the two other streams of ammonia (stream a) and the substream or overall stream (stream b) from the reactor circulation and thus dissolving it.

The advantage of metering the PN as a melt or solid into the liquid ammonia and the substream, consisting virtually of xylylenediamine and ammonia, of the reactor circulation is that the phthalonitrile is already diluted immediately after the mixing and is present at a temperature distinctly below 120° C., so that an undesired reaction between nitrile and product can be substantially suppressed. Moreover, the melt can be metered at a pressure which is less than the reactor pressure, as a result of which a less expensive melt pump can be used. The solution can then subsequently be compressed to the desired reactor pressure. Use of a substream of the reactor circulation allows the ammonia present therein to be used again to dissolve phthalonitrile without preceding workup. It is thus possible to set the ratio of phthalonitrile and ammonia optimal for the reaction. The majority of the ammonia is thus circulated and only the small amount of ammonia which is conducted to workup with the reaction product (e.g. stream [16] in FIG. 3) has to be worked up by pressure distillation. An additional amount of fresh or worked-up ammonia to dissolve the phthalonitrile at low temperature is not required. It is thus possible to carry out the dissolution of phthalonitrile at low temperature and simultaneously to work up only the minimum amount of ammonia. The requirements on the machines and apparatus used correspond to the standard supplied, by virtue of which apparatus and maintenance costs can be kept small.

The conduct and dissolution of the phthalonitrile into the two liquid streams a and b requires a mixing unit, preferably a mixing nozzle or a mixing vessel. It is possible first to mix the streams of ammonia (stream a) and the mixture of ammonia and xylylenediamine (stream b), and then to dissolve PN, for example IPN, in this mixture. However, it is also possible to feed all three streams simultaneously and separately to the mixing unit.

A mixing nozzle can be realized in the simplest case by a pipeline T-piece. The nozzle mouth preferably has a narrowing.

When a mixing nozzle is used, two or more streams are fed separately, and mixed and homogenized in the attached tube on the basis of the prevailing turbulence. Advantageously, a static mixer may additionally be attached downstream. However, no additional apparatus, for instance a stirred tank for dissolving (solid or liquid) phthalonitrile in a solvent, is required.

Preferably, the mixing unit, at the location of the phthalonitrile feed into streams a and b, is heated to a temperature in the range from 1 to 60° C., particularly in the range from 5 to 40° C. and in particular in the range from 7 to 25° C. above the melting point of the phthalonitrile used.

The PN is preferably fed virtually at an absolute pressure between 15 bar and the reactor pressure. The minimum pressure arises from the particularly preferred boundary condition that no evaporation occurs in the course of mixing and at the mixing temperature which is established, but rather the mixture remains in liquid form. It is thus dependent upon the starting temperature and the quantitative ratio of the components to be mixed. Mixing at low pressure, for example in the range from 25 to 40 bar, offers the advantage that the melt pump does not have to be designed for the distinctly higher reactor pressure. In this case, the PN solution in ammonia, however, still has to be compressed to the reactor pressure by means of a high-pressure pump, albeit a simple one in construction terms.

More preferably, the liquid phthalonitrile is sprayed into streams a and b by means of a mixing nozzle as the mixing unit.

A preferred embodiment of the mixing nozzle is shown in the appendix in FIG. 1. The mixing nozzle can be heated, for example, with steam, heat carrier oil or else electrically.

Figure 2:
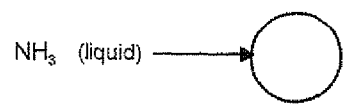
FIG. 2 is a representation of suitable ammonia feed points via nozzle mounting locations in accordance with various embodiments of the present invention.
Figure 2:
Figure 2:
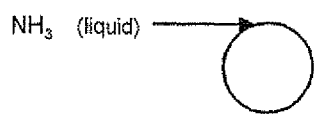
Figure 2:

The liquid ammonia can be fed via one or more radially or tangentially mounted nozzles, for example as shown in FIG. 2.

What is important is the locally high flow rate (high impulse stream and turbulence), so that rapid mixing (homogenization) occurs. In the case of laminar flow, the mass transfer is not sufficient for homogenization and the streams are only insufficiently mixed (streak formation).

Suitable mixing nozzles are described, for example, in Ullmann's Encyclopedia of Industrial Chemistry, 5th edition, Vol. B4, pages 565-569.

Figure 3:
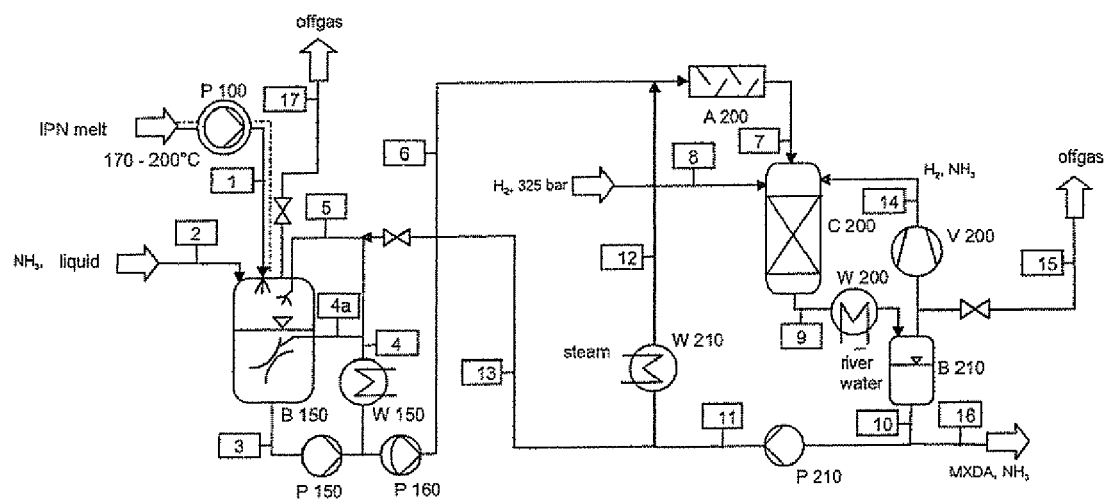
FIG. 3 is a schematic diagram in accordance with an embodiment of the present invention.

A further particularly preferred mixing unit is a mixing vessel with circulation stream, as shown, for example, in FIG. 3.

The PN melt (stream [1], FIG. 3) is fed to the vessel B 150 separately from the other streams. Liquid ammonia (stream [2]), a substream (stream [13]) from the circulation stream around the hydrogenation reactor and the circulation stream (stream [4]) around the mixing vessel may be fed to the mixing vessel B 150 either separately or combined and together. Alternatively, as shown in FIG. 3, the ammonia (stream [2]) is separated and stream [4] and [13] are conducted combined into vessel B 150. The different feed streams may be sprayed (atomized), for example, in each case with the aid of nozzles or combined and mixed in another way. To improve the turbulence in the mixing vessel, a substream of stream [4] can be branched off and conducted via a mixing nozzle to the vessel (stream [4a]).

For each stream, one or else more nozzles may be used. The liquid ammonia may likewise be sprayed. If the circulation stream (stream [4]) around the mixing vessel is dispensed with, ammonia is sprayed in place of the solution. The solution from the circulation stream or the liquid ammonia is preferably sprayed in such a way that a majority of the gas space is covered. In particular, the solution or the ammonia is sprayed over the entire cross-sectional area, so that some of the solution or some of the liquid ammonia runs down the vessel walls and forms a liquid film. Solid deposits are thus prevented. The PN is likewise sprayed, but preferably within a narrower spray cone which is disposed substantially within the solution or ammonia spray cone. Advantageously, this can be realized, for example, by the PN nozzle being mounted centrally and, for example, three or more nozzles for solution or ammonia being arranged around it. The small PN droplets mix and dissolve spontaneously in the ammonia or in the solution. The mixture is conveyed out of the mixing vessel with the pump P 150 and can be adjusted to the desired temperature in a heat transferrer W 150. Depending on the mixing ratio and temperatures of the individual substreams, heating or cooling is necessary in W 150 in order to obtain the desired temperature. Subsequently, the mixture (stream [6]) is compressed to reactor pressure with the pump P 160.

Recycling the mixture back to the mixing vessel (stream [4]) downstream of the heat transferrer W 150 and spraying it by means of nozzles is advantageous owing to the discharge of heat. However, it is also possible to dispense with the circulation stream. In that case, flow rate [3] equates to flow rate [6], and flow rate [4] becomes zero. The operating pressure of the vessel is dependent upon the process conditions, especially upon the temperature. At a given feed temperature of the fresh ammonia (stream [2]), of the PN melt (stream [1]) and of the substream from the reactor circulation (stream [3]), variation of the circulation stream around the mixing vessel (stream [4]) and adjustment of the temperature of the circulation stream downstream of the cooler W 150 allows the mixing temperature in the vessel to be selected within certain limits, especially taking into account the temperature-dependent solubility of PN in a mixture of ammonia and xylylenediamine. Thus, the appropriate vapor pressure is then established over the solution in the gas space. If appropriate, it is also possible for inert gas, for example nitrogen or hydrogen, to be present in the gas space. The hydrogen is introduced dissolved in the stream [13] and released in the course of decompression to mixing vessel pressure. An offgas stream [17] can thus be discharged from the mixing vessel if required. Advantageously, the pressure in the vessel B 150 is not more than 40 bar, preferably not more than 30 bar, more preferably not more than 25 bar, so that inexpensive apparatus and machines can be used. In that case, the high-pressure pump P 160 compresses the solution to the reactor pressure for the hydrogenation. Stream [6] is then mixed with the remaining circulation stream around the reactor (stream [12]), for example with the aid of a static mixer A 200, as shown in FIG. 3. When the complete stream [11] (stream [13] corresponds to stream [11]; stream [12]=0) is conducted to the mixing vessel, stream [6] is conducted directly to the reactor.

Instead of the mixing vessel, it is also possible to use a stirred tank whose temperature can be adjusted by means of a jacket or an external circulation stream with heat transferrer.

In a preferred embodiment of the process according to the invention, the resulting liquid mixture of ammonia, phthalonitrile and xylylenediamine is conducted into the circulation stream around the hydrogenation reactor, the circulation stream consisting to an extent of greater than 93% by weight of liquid ammonia and xylylenediamine.

In an advantageous embodiment of the process according to the invention, furthermore, the mixture conducted to the hydrogenation reactor does not comprise any further solvent for phthalonitrile.

The phthalonitrile conversion in the hydrogenation reactor or in the hydrogenation reactor battery in single pass is preferably greater than 99%, particularly greater than 99.5%, very particularly greater than 99.9%, in particular greater than 99.95%, very particularly greater than 99.97%. In the hydrogenation reactor, the reaction is conducted virtually to full conversion by virtue of appropriate adjustment of the reaction conditions (pressure, temperature, molar ratios of PN, $NH_3$ and $H_2$, catalyst, flow rates, residence time in the reactor).

The liquid circulation stream, branched off at the reactor outlet, around the hydrogenation reactor preferably consists to an extent of greater than 94% by weight, in particular greater than 95% by weight, very particularly greater than 96% by weight, even more particularly greater than 97% by weight of liquid ammonia and xylylenediamine; the remainder is formed by secondary components.

Secondary components in the liquid circulation stream around the hydrogenation reactor or the hydrogenation reactor battery (circulation stream) may be by-products formed in the reaction and also dissolved gases and secondary components conducted with the phthalonitrile, for example solvent residues of an upstream PN quench stage (e.g. tolunitrile, benzonitrile), but preferably no further solvent, for example organic solvent, for phthalonitrile.

The circulation stream, branched off at the reactor outlet, around the hydrogenation reactor or the hydrogenation reactor battery comprises preferably in the range from 25 to 90% by weight, particularly from 30 to 70% by weight, in particular from 45 to 60% by weight of liquid ammonia.

The portion of the liquid reactor effluent which is recycled directly or indirectly, preferably continuously, to the reactor inlet as the circulation stream (see, for example, stream [11] in FIGS. 3 and 4; or else, for example, the sum of streams 12 and 13 in FIGS. 3 and 4) makes up preferably from 20 to 95% by weight, particularly from 50 to 92% by weight, in particular from 75 to 90% by weight of the entire liquid reactor effluent.

The weight ratio of fresh phthalonitrile feed stream+ammonia feed stream (for example sum of streams [1] and [2] in FIGS. 3 and 4) to circulation stream around the hydrogenation reactor (for example stream [11] in FIGS. 3 and 4) is preferably in the range from 0.05 to 5, particularly in the range from 0.1 to 2.0, in particular in the range from 0.15 to 1.0.

The reaction temperature is preferably in the range from 40 to 150° C., more preferably from 50 to 135° C., in particular from 60 to 130° C.

The amount of ammonia, the amount of the circulation stream [e.g. stream 11] and the reactor feed temperature are adjusted such that the reactor outlet temperature does not exceed the desired maximum value (e.g. 130° C.), since by-products are formed to an enhanced extent with increasing temperature. The reactor feed temperature is adjusted (for example by an additional heat transferrer or, preferably, by suitable adjustment of the temperature of the streams to be mixed) such that the reaction proceeds sufficiently rapidly and full conversion is achieved. When initially only partial conversion is achieved, the feed temperature to the reactor is increased such that full conversion is achieved. Variation of the circulation flow rate around the hydrogenation reactor or the hydrogenation reactor battery and fresh flow rate of ammonia thus makes it possible to adjust both the inlet temperature and, within certain limits, the outlet temperature of the reactor and to adjust them optimally to the proceeding reactions and thus to optimize the XDA yield.

The hydrogenation is carried out preferably at absolute pressure in the range from 100 to 300 bar, in particular from 120 to 220 bar, very particularly from 150 to 200 bar.

For the hydrogenation, catalysts and reactors known to those skilled in the art (especially tubular reactors or tube bundle reactors; fixed bed or suspension mode) may be employed.

For the fixed bed catalyst mode, both liquid phase mode and trickle mode are possible. Preference is given to trickle mode.

The reactor or the reactors is/are preferably operated adiabatically, while the heat of reaction which arises is removed via a cooler installed in the circulation stream and optionally with the cycle gas used. This additionally increases the selectivity of the reaction by virtue of the further suppression of by-products.

Alternatively, it is also possible to use a cooled reactor or reactors, for example a tube bundle reactor.

Preference is given to catalysts which comprise cobalt and/or nickel and/or iron, as an unsupported catalyst or on an inert support. It is also possible here to use a combination of different catalysts.

Particular preference is given to carrying out the hydrogenation over a manganese-doped unsupported cobalt catalyst.

Suitable catalysts are, for example, Raney nickel, Raney cobalt, unsupported Co catalyst, titanium-doped cobalt on support (JP-A-2002 205980), Ni on $SiO_2$ support (WO-A-2000/046179), Co/Ti/Pd on $SiO_2$ support (CN-A-1 285 343, CN-A-1 285 236) and nickel and/or cobalt on zirconium dioxide support (EP-A1-1 262 232).

Examples of further suitable catalysts can be found, for example, in the applications GB-A-852,972 (equivalent: DE-A-11 19 285) (BASF AG), DE-A-12 59 899 (BASF AG) and the U.S. Pat. Nos. 3,069,469 (California Research Corp.) and 4,482,741 (UOP Inc.).

Particularly preferred catalysts are the unsupported cobalt catalysts doped with Mn, P, and alkali metal (Li, Na, K, Rb, Cs) disclosed in EP-A1-742 045 (BASF AG). The catalytically active composition of these catalysts consists, before reduction with hydrogen, of from 55 to 98% by weight, in particular from 75 to 95% by weight of cobalt, from 0.2 to 15% by weight of phosphorus, from 0.2 to 15% by weight of manganese and from 0.05 to 5% by weight of alkali metal, especially sodium, calculated in each case as the oxide.

Further suitable catalysts are the catalysts disclosed in EP-A-963 975 (BASF AG), whose catalytically active composition before treatment with hydrogen comprises from 22 to 40% by weight of $ZrO_2$, from 1 to 30% by weight of oxygen compounds of copper calculated as CuO, from 15 to 50% by weight of oxygen compounds of nickel calculated as NiO, where the molar Ni:Cu ratio is greater than 1, from 15 to 50% by weight of oxygen compounds of cobalt calculated as CoO, from 0 to 10% by weight of oxygen compounds of aluminum and/or manganese, calculated as $Al_2O_3$ and $MnO_2$ respectively, and no oxygen compounds of molybdenum, for example the catalyst A disclosed in loc. cit., page 17, with the composition 33% by weight of Zr, calculated as $ZrO_2$, 28% by weight of Ni calculated as NiO, 11% by weight of Cu calculated as CuO and 28% by weight of Go calculated as CoO, the catalysts disclosed in EP-A-696 572 (BASF AG), whose catalytically active composition before reduction with hydrogen comprises from 20 to 85% by weight of $ZrO_2$, from 1 to 30% by weight of oxygen compounds of copper calculated as CuO, from 30 to 70% by weight of oxygen compounds of nickel calculated as NiO, from 0.1 to 5% by weight of oxygen compounds of molybdenum calculated as $MoO_3$, and from 0 to 10% by weight of oxygen compounds of aluminum and/or manganese, calculated as $Al_2O_3$ and $MnO_2$ respectively, for example the catalyst disclosed in loc. cit., page 8, with the composition 31.5% by weight of $ZrO_2$, 50% by weight of NiO, 17% by weight of CuO and 1.5% by weight of $MoO_3$, and the catalysts described in WO-A-99/44984 (BASF AG) and comprising (a) iron or a compound based on iron or mixtures thereof, (b) from 0.001 to 0.3% by weight, based on (a), of a promoter based on 2, 3, 4 or 5 elements from the group of Al, Si, Zr, Ti, V, (c) from 0 to 0.3% by weight, based on (a), of a compound based on an alkali metal and/or alkaline earth metal, and (d) from 0.001 to 1% by weight, based on (a), of manganese.

Figure 4:
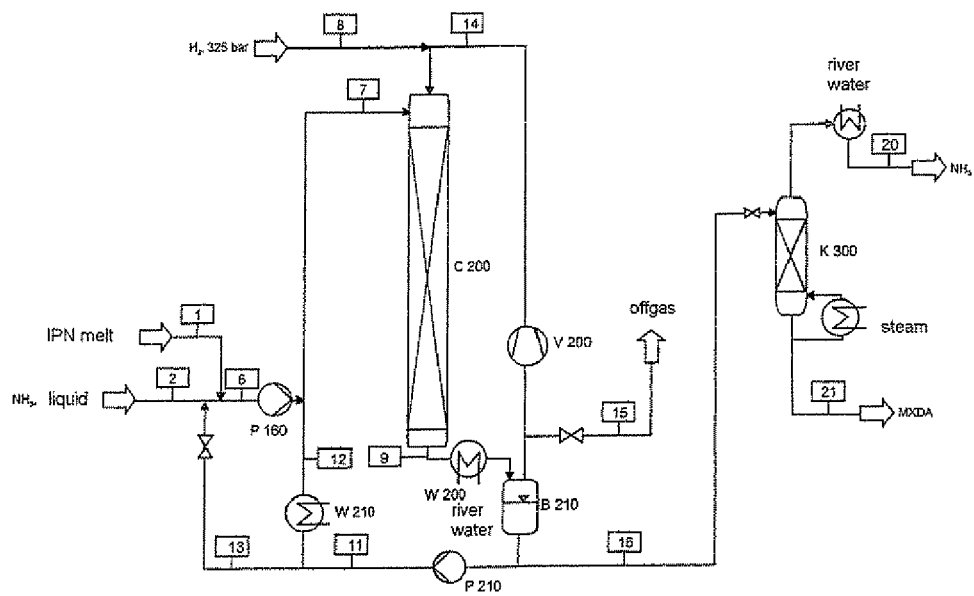
FIG. 4 is a schematic diagram in accordance with an embodiment of the present invention.

The process according to the invention can be performed, for example, as follows:

FIG. 4 shows one possible arrangement of the hydrogenation reactor including the optional circulation stream [12] and a heat transferrer (W 210). The phthalonitrile melt is fed as stream [1], and mixed with the liquid ammonia [2] and the substream from the circulation stream around the reactor [13]. The mixture is either mixed with the optionally present circulation stream [12] or conducted directly to the reactor. For better mixing with the circulation stream, it is possible for example, to use a static mixer.

Hydrogen and, if appropriate, cycle gas may be heated to the desired reactor feed temperature by means of an optional heat transferrer. Gas and liquid may be conducted to the reactor together or, preferably, separately. The temperature of the streams to be mixed is preferably adjusted by means of heat transferrers such that no further heat transferrer is required beyond the mixing point. In the reactor, the hydrogenation is effected virtually quantitatively, so that virtually no further phthalonitrile is present in the reaction effluent. The reaction effluent can then be cooled, and gas and liquid are separated under pressure in a high-pressure separator. In circulation liquid mode, a portion of the liquid from the reaction effluent is circulated without workup (stream [11]). Apart from this, the reaction effluent is fed partly to the mixing vessel (stream [13] and partly to the workup (stream [16]). A portion of the gas can be discharged (stream [15]) in order to prevent the accumulation of inerts (CO, $N_2$, $CH_4$, noble gases, etc.). The majority of the gas is recycled to the reactor inlet via a compressor. In the case of not too high a pressure drop in the reactor, it is preferably also possible for this purpose to use an ejector nozzle ("water-jet pump"). Overall, the amount of cycle gas can be varied within wide ranges, for instance from several times the amount of fresh gas down to zero (mode without cycle gas). The cycle gas mode is favorable for loading the reactor sufficiently on the gas side for good mass transfer and for providing a sufficient entrainment stream for inert gases in order to be able to discharge them at the reactor outlet. In addition, some of the heat of reaction can be removed with the gas stream. With increasing temperature, an increasing amount of ammonia evaporates, which further enhances the cooling effect of the cycle gas. The reaction effluent (stream [16]) is then first fed to a pressure distillation in which liquid ammonia is obtained overhead (stream [20]) and substantially ammonia-free, crude xylylenediamine is obtained via the bottom (stream [21]), and it is possible to feed the ammonia in condensed form back to the hydrogenation stage (as stream [2]). The crude xylylenediamine is purified further, for example, by distillation.

In the process according to the invention, the larger the substream [13] branched off from stream [11] to the mixing vessel, the larger the size of the weight ratio of the fresh feeds of dinitrile and ammonia (for example, according to FIG. 3 or 4, the ratio of stream [1] to stream [2]) that can be selected. Depending on the amount of stream [2], the lower limit of stream [13] results from the solubility of phthalonitrile in the mixture of liquid ammonia and phthalonitrile at the given temperature (for example, the solubility of IPN in $NH_3$ at 60° C. is approx. 44% by weight, and approx. 15% by weight in meta-xylylenediamine. In a mixture of approximately equal parts by mass of meta-xylylenediamine and liquid ammonia, the solubility is approx. 30% by weight).

The feed stock weight ratio of dinitrile (stream [1]) to ammonia (stream [2]) is from 1:0.5 to 1:2, preferably from 1:0.7 to 1:1.5, more preferably from 1:0.9 to 1:1.2. The weight ration of the recycled substream [e.g. stream 13] from the circulation stream to the fresh feed (sum of fresh phthalonitrile and ammonia feed stream, for example streams [1] and [2]) is preferably from 1:0.3 to 1:2, preferably from 1:0.5 to 1:1.5, more preferably from 1:0.7 to 1:1.1.

In the mode without direct circulation liquid (stream [12] =0) around the hydrogenation reactor or hydrogenation reactors, i.e. when the stream which is drawn off at least as a substream from the circulation stream around the hydrogenation reactor (stream b) is the entire circulation stream, the feed stock weight ratio of dinitrile to ammonia is preferably from 1:0.5 to 1:2, preferably from 1:0.7 to 1:1.5, more preferably from 1:0.9 to 1:1.2, i.e. it is preferably the same as in the case with direct circulation around the hydrogenation reactor as described above.

The weight ratio of the recycled substream [e.g. stream 13] from the reactor effluent to the fresh feed (sum of fresh phthalonitrile and ammonia feed stream, for example sum of streams [1] and [2]) is, in this case, from 2:1 to 10:1, preferably from 3:1 to 8:1, more preferably from 4.5:1 to 6:1.

Isolation of the XDA:

After the hydrogenation, the ammonia used is removed, for example distilled off.

Preference is given to purifying the xylylenediamine by distilling off lower-boiling by-products (at the same pressure) overhead and distillatively removing higher-boiling impurities via the bottom.

Particular preference is given to the method in which, after the hydrogenation, the ammonia and any low-boiling by-products are distilled off overhead and then higher-boiling impurities are removed distillatively via the bottom from the xylylenediamine.

In a particular embodiment, lower- and higher-boiling by-products can also be removed in a side draw column or dividing wall column, in which case pure xylylenediamine is obtained via a liquid or gaseous side draw.

Depending on the desired purity, the product (XDA) is additionally extracted with an organic solvent, preferably an aliphatic hydrocarbon, especially a cycloaliphatic hydrocarbon, very particularly cyclohexane or methylcyclohexane.

This purification by extraction can be effected, for example, according to DE-A-1 074 592 (BASF AG).

EXAMPLES

In the examples, the mixture of the streams is calculated (by addition of the individual stream amounts); the hydrogenation of the resulting mixture was carried out experimentally, with unconnected circulation systems.

Example 1

90 g/h of molten IPN (commercial IPN flakes which had been molten by heating to approx. 170° C.) were mixed in a vessel at 60° C. with 178 g/h from circulation stream [13] and 94 g/h of fresh ammonia [2] and thus dissolved. This forms a solution comprising 25% by weight of IPN. At 60° C., the solubility of IPN in the mixture is about 30% by weight. The mixing temperature can be adjusted by virtue of the temperature and the flow rate of the circulation stream [4]. When ammonia is fed at 30° C., the circulation stream [13] at 50° C. and IPN at 170° C., stream [4] may, for example, be 470 g/h at 58° C. in order to come to the mixing temperature of 60° C., not taking into account heat losses. The boiling pressure in the mixing vessel is then 23.3 bar (abs.), i.e., above this pressure, the mixture remains liquid and no evaporation of ammonia takes place. The solution is conducted into a circulation stream (approx. 839 g/h) consisting of the liquid recycle stream of the reactor effluent. The IPN concentration at the reactor inlet is thus 7.5% by weight. 50 mol of $NH_3$ are present at the reactor inlet per mole of IPN.

The resulting reaction mixture was hydrogenated continuously in a tubular reactor over an unsupported cobalt catalyst at 90° C. and 200 bar. The portion of the reactor effluent drawn off was freed of the majority of the amount of ammonia in an ammonia column and analyzed by GC. At full conversion of the IPN used (i.e. conversion greater than 99.95%; no further reactant detectable by GC), the selectivity was 92%.

In subsequent distillation steps, first residual ammonia and low-boiling secondary components were removed. After the high-boiling impurities had been removed via the bottom, MXDA was obtained as the top product of a distillation column in a purity of more than 99.9% by weight.

Example 2

90 g/h of molten IPN (commercial IPN flakes which had been molten by heating to approx. 170° C.) were mixed in a vessel at 60° C. with 320 g/h from circulation stream [13] and 40 g/h of fresh ammonia [2] and thus dissolved. This forms a solution comprising 20% by weight of IPN. At 60° C., the solubility of IPN in the mixture is about 25% by weight. The mixing temperature can be adjusted by virtue of the temperature and the flow rate of the circulation stream [4]. When ammonia is fed at 30° C., the circulation stream [13] at 45° C. and IPN at 170° C., stream [4] may, for example, be 527 g/h at 58° C. in order to come to the mixing temperature of 60° C., not taking into account heat losses. The boiling pressure in the mixing vessel is then 20.2 bar (abs.), i.e., above this pressure, the mixture remains liquid and no evaporation of ammonia takes place. The solution is conducted into a circulation stream (approx. 750 g/h) consisting of the liquid recycle stream of the reactor effluent. The IPN concentration at the reactor inlet is thus 7.5% by weight. 30 mol of $NH_3$ are present at the reactor inlet per mole of IPN.

The resulting reaction mixture was hydrogenated continuously in a tubular reactor over an unsupported cobalt catalyst at 90° C. and 200 bar. The portion of the reactor effluent drawn off was freed of the majority of the amount of ammonia in an ammonia column and analyzed by GC. At full conversion of the IPN used (i.e. conversion greater than 99.95%; no further reactant detectable by GC), the selectivity was 88%.

In subsequent distillation steps, first residual ammonia and low-boiling secondary components were removed. After the high-boiling impurities had been removed via the bottom, MXDA was obtained as the top product of a distillation column in a purity of more than 99.9% by weight.

What is claimed is:

1. A process for preparing a xylylenediamine by continuous hydrogenation, the process comprising:
    introducing a liquid circulation stream comprising a phthalonitrile and ammonia into a reactor to continuously hydrogenate the phthalonitrile in the presence of a heterogeneous catalyst and the ammonia such that a reactor effluent comprising the xylylenediamine is formed;
    drawing off a portion of the reactor effluent to provide a first recycle stream;
    mixing at least a portion of the first recycle stream in a mixing unit with liquid ammonia and fresh phthalonitrile in solid or molten form to provide a second recycle stream; and
    recycling the second recycle stream to the liquid circulation stream.

2. The process according to claim 1, wherein the second recycle stream and any remaining unmixed portion of the first recycle stream are both recycled to the liquid circulation stream.

3. The process according to claim 1, wherein the phthalonitrile comprises isophthalonitrile.

4. The process according to claim 1, wherein at least a portion of the mixing unit where the fresh phthalonitrile is fed in is heated to a temperature of 1 to 60° C. above the melting point of the phthalonitrile.

5. The process according to claim 1, wherein the mixing unit comprises a mixing nozzle and the fresh phthalonitrile is sprayed into the mixing unit.

6. The process according to claim 1, wherein the mixing unit comprises a mixing vessel; and wherein the fresh phthalonitrile, liquid ammonia, and the portion of the first recycle stream are sprayed into the mixing vessel.

7. The process according to claim 1, wherein the fresh phthalonitrile is introduced into the mixing unit in solid form and mixed with the liquid ammonia and the portion of the first recycle stream.

8. The process according to claim 1, wherein the liquid ammonia and the portion of the first recycle stream are mixed prior to mixing with the fresh phthalonitrile.

9. The process according to claim 1, wherein a combined amount of the liquid ammonia and the xylylenediamine in the liquid circulation stream introduced into the reactor is greater than 93% by weight.

10. The process according to claim 1, wherein the liquid circulation stream does not comprise any additional solvent for phthalonitrile.

11. The process according to claim 1, wherein the phthalonitrile conversion in the hydrogenation reactor in a single pass is greater than 99%.

12. The process according to claim 1, wherein the phthalonitrile conversion in the hydrogenation reactor in a single pass is greater than 99.5%.

13. The process according to claim 1, wherein a combined amount of the liquid ammonia and the xylylenediamine in the liquid circulation stream introduced into the reactor is greater than 94% by weight.

14. The process according to claim 1, wherein the liquid circulation stream introduced into the reactor comprises 25 to 90% by weight of liquid ammonia.

15. The process according to claim 1, wherein the first recycle stream is 20 to 95% by weight of the overall reactor effluent.

16. The process according to claim 1, wherein a weight ratio of the fresh phthalonitrile and liquid ammonia to the first recycle stream is 0.05 to 5.

17. The process according to claim 1, wherein a weight ratio of the portion of the first recycle stream mixed in the mixing unit to the combined fresh phthalonitrile and liquid ammonia is 1:0.3 to 1:2.

18. The process according to claim 1, wherein the entire first recycle stream is mixed in the mixing unit with the fresh phthalonitrile in solid or molten form and the liquid ammonia to provide the second recycle stream; and wherein a weight ratio of the first recycle stream to the combined fresh phthalonitrile and liquid ammonia is 2:1 to 10:1.

19. The process according to claim 1, wherein the hydrogenation is carried out at a temperature of 40 to 150° C.

20. The process according to claim 1, wherein the hydrogenation is carried out at an absolute pressure of 100 to 300 bar.

21. The process according to claim 1, wherein the heterogenous catalyst comprises at least one selected from the group consisting of Ni, Co, Fe and mixtures thereof.

22. The process according to claim 1, wherein the heterogenous catalyst comprises a manganese-doped unsupported cobalt catalyst.

23. The process according to claim 1, wherein the heterogenous catalyst is arranged as a fixed bed in a tubular reactor or tube bundle reactor.

24. The process according to claim 23, wherein the hydrogenation reactor is operated in trickle mode.

25. The process according to claim 1, wherein the hydrogenation reactor is operated adiabatically.

26. The process according to claim 1, wherein heat is removed in a cooler from the liquid circulation stream.

27. The process according to claim 1, wherein the hydrogenation reactor comprises a hydrogenation reactor battery.

28. The process according to claim 1, further comprising subjecting at least a second portion of the reactor effluent to purification to provide a purified xylylenediamine, the purification comprising distilling the second portion to remove ammonia and lower-boiling by-products overhead and higher-boiling impurities below.

29. The process according to claim 28, wherein the purified xylylenediamine, after the distillation, is further purified by extraction with an organic solvent.

30. The process according to claim 29, wherein the organic solvent comprises cyclohexane, methylcyclohexane or a mixture thereof.

* * * * *